United States Patent
Naglreiter et al.

(10) Patent No.: US 6,379,329 B1
(45) Date of Patent: Apr. 30, 2002

(54) DETACHABLE BALLOON EMBOLIZATION DEVICE AND METHOD

(75) Inventors: Brett E. Naglreiter, Hollywood; Donald K. Jones, Lauderhill, both of FL (US)

(73) Assignee: Cordis Neurovascular, Inc., Miami Lakes, FL (US)

( * ) Notice: Subject to any disclaimer, the term of this patent is extended or adjusted under 35 U.S.C. 154(b) by 76 days.

(21) Appl. No.: 09/585,086

(22) Filed: Jun. 1, 2000

Related U.S. Application Data
(60) Provisional application No. 60/137,190, filed on Jun. 2, 1999.

(51) Int. Cl.[7] .............................................. A61M 29/00
(52) U.S. Cl. ................ 604/99.02; 604/99.02; 604/95.02; 604/101.02; 604/103.01; 604/104; 604/913
(58) Field of Search ........................ 604/95.02, 95.03, 604/99.02, 101.02, 101.01, 101.03, 103.01, 103, 103.02, 103.05, 104, 913

(56) References Cited

U.S. PATENT DOCUMENTS

| | | |
|---|---|---|
| 4,085,757 A | 4/1978 | Pevsner |
| 4,517,979 A | 5/1985 | Pecenka |
| 4,545,367 A | 10/1985 | Tucci |
| 4,638,803 A | 1/1987 | Rand |
| 4,836,204 A | 6/1989 | Landymore et al. |
| 5,041,090 A | 8/1991 | Scheglov et al. |
| 5,258,042 A | 11/1993 | Mehta |
| 5,443,478 A | 8/1995 | Purdy |
| 5,451,235 A | 9/1995 | Lock et al. |
| 5,634,936 A | 6/1997 | Liden et al. |
| 5,725,535 A | * 3/1998 | Hegde et al. ....... 604/101.01 X |
| 5,827,171 A | * 10/1998 | Dobak, III et al. ........... 600/16 |
| 6,165,193 A | 12/2000 | Greene, Jr. et al. |

* cited by examiner

Primary Examiner—Anhtuan T. Nguyen
(74) Attorney, Agent, or Firm—Henry W. Collins

(57) ABSTRACT

An endovascular aneurysm occlusion device comprising a detachable balloon assembly. The balloon assembly is comprised of an outer balloon and an inner balloon. The outer balloon is formed from a porous material. The occlusion device is expanded within an aneurysm and adhesive material is injected into and perfused through the outer balloon. The adhesive material forms a bond between the aneurysm, the outer balloon, and the inner balloon. The inner balloon is then deflated, which acts to reduce the size of the aneurysm.

3 Claims, 4 Drawing Sheets

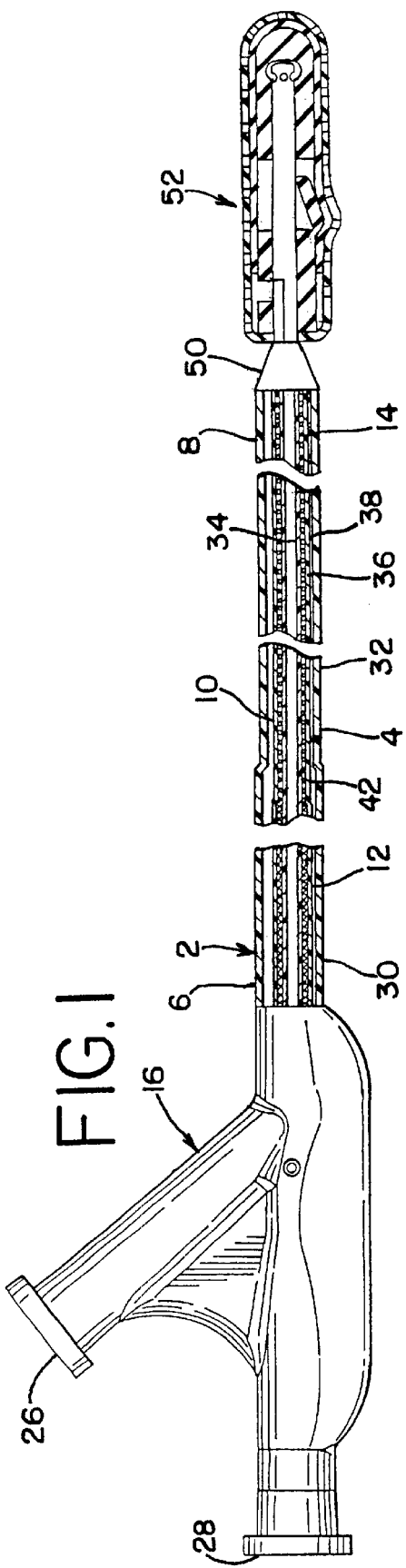

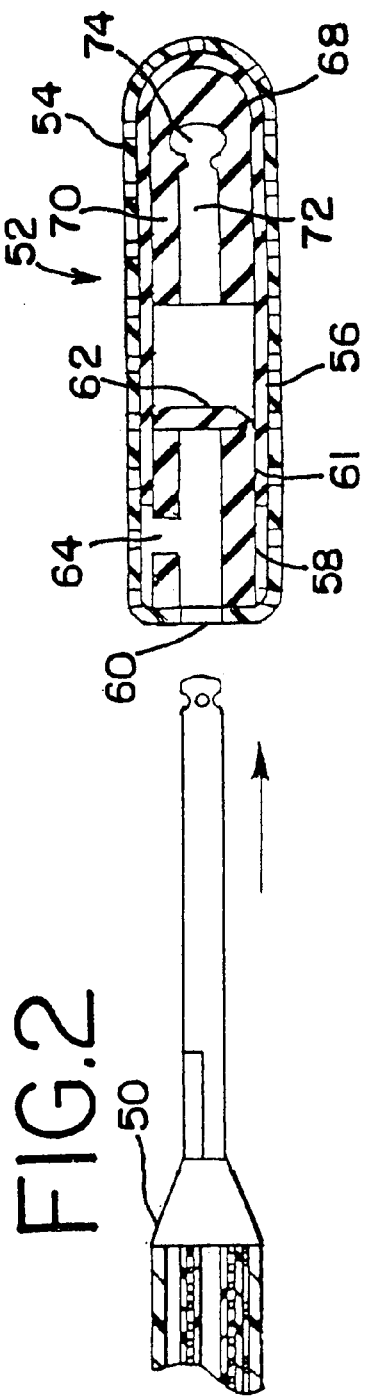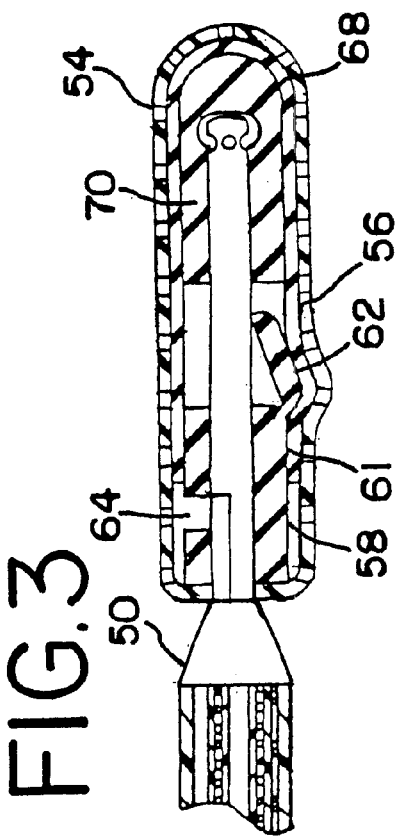

DETACHABLE BALLOON EMBOLIZATION DEVICE AND METHOD

CROSS-REFERENCE TO A RELATED APPLICATION

This application claims the benefit of U.S. Provisional Application No. 60/137,190 filed Jun. 2, 1999, the disclosure of which is incorporated herein by reference.

BACKGROUND OF THE INVENTION

1. Field of the Invention

This invention relates generally to vascular occlusion devices and particularly to a vascular occlusion device which is used to reduce the size of an aneurysm.

2. Description of the Prior Art

A number of techniques have been developed for the treatment of aneurysms. Initially, aneurysms were treated by invasive surgical methods. A physician would need to surgically remove the aneurysm from the parent vessel. Such procedures prove more challenging and carry a greater risk of impairment due to collateral damage when the aneurysm occurs in sensitive areas of the body, such as the brain.

Less invasive techniques have been developed. These techniques involve filling the aneurysm with material to prevent the aneurysm from growing in size. The aneurysm may be filled with a variety of structures, such as coils or balloons. Frequently, the structures used to fill an aneurysm are coated with a thrombogenic material, such as in U.S. Pat. No. 4,638,803 to Rand.

Polymers have also been used to fill aneurysms. For example, U.S. Pat. No. 5,041,090 to Scheglov, et al., discloses an aneurysm occluding device. A pair of balloons, one disposed within the other, is placed within an aneurysm. The inner balloon is expanded to force the outer balloon to contact the wall of the aneurysm. The inner balloon is filled with a polymer and the outer balloon is filled with an adhesive which flows through perforations in the outer balloon. The aneurysm adheres to the outer balloon and the layer of adhesive forms a bond between the outer balloon and the inner balloon.

Such a procedure requires the use of a detachable balloon. Some examples of detachable balloon designs can be found in U.S. Pat. No. 4,517,979 to Pecenka, U.S. Pat. No. 4,545,367 to Tucci, and U.S. Pat. No. 4,085,757 to Pevsner. In each case, a single balloon has a sealing valve assembly which seals the balloon when the catheter is removed.

The filling material, whether coils or polymers, are introduced into the body using catheters. The catheters are navigated through blood vessels to the site of the aneurysm. Such endovascular techniques are often preferred to the traditional invasive procedures due to reduced post-operative complications and recovery time.

Filling an aneurysm is not always an adequate solution, however. In some cases, the size of the aneurysm interferes with the surrounding tissue or other blood vessels. In these cases, filling the aneurysm does not reduce the "mass effect" caused by the aneurysm. Therefore, the prior art does not always produce adequate results.

SUMMARY OF THE INVENTION

In accordance with the present invention, there is an endovascular aneurysm occlusion device comprising a catheter. The catheter includes an outer tubular member having a proximal end, a distal end, and a lumen extending therethrough. The catheter also includes an inner tubular member having a proximal end, a distal end, and a lumen extending therethrough. The inner tubular member is coaxially disposed within the lumen of the outer tubular member.

The occlusion device also includes a balloon assembly having an outer balloon having an outer wall defining an interior region and an inner balloon having an outer wall defining an interior region. The inner balloon is disposed within the interior region of the outer balloon.

The balloon assembly also includes a valve assembly. The valve assembly extends through the wall of the outer balloon and an adjacent, portion of the wall of the inner balloon. The valve assembly has a passageway therethrough and a valve means disposed in the passageway. The distal end of the outer and inner tubular members of the catheter extending into the passageway, and the valve means is operative to permit the passage of the catheter through the valve assembly but preventing the flow of fluid through said valve assembly when the catheter is withdrawn from said valve assembly.

The occlusion device also includes a hub having a first lumen and a second lumen. Each lumen extends through the hub connector. The hub is mounted to the proximal end of the outer tubular member and the proximal end of the inner tubular member such that the first lumen of the hub is in fluid communication with the lumen of the outer tubular member and the second lumen of the hub is in fluid communication with the lumen of the inner tubular member.

In accordance with another aspect of the present invention, the outer balloon is formed of a porous material.

In accordance with still another aspect of the present invention, there is a method for occluding an aneurysm by the use of an occlusion device comprising a balloon assembly which includes an outer balloon, an inner balloon, and a valve assembly. The outer balloon is formed from a porous material and the inner balloon is disposed within the outer balloon. The valve assembly extends through a wall of the inner balloon and an adjacent wall of the outer balloon. A catheter has its distal end removably disposed within the valve assembly. The method comprises the steps of: positioning the balloon assembly within an aneurysm; inflating the inner balloon such that the inner balloon makes contact with the outer balloon to thereby force the outer balloon into contact with the aneurysm; introducing an adhesive material into a region between the inner balloon and the outer balloon thereby causing the inner balloon to become bonded to the outer balloon; perfusing the adhesive material through the porous material of the outer balloon thereby causing the outer balloon to become bonded to the aneurysm; deflating the inner balloon thereby causing the outer balloon to contract which, in turn, reduces the size of the aneurysm; and, detaching the catheter from the balloon assembly thereby causing the valve assembly to close and thereby causing the inner balloon to remain in a deflated state.

BRIEF DESCRIPTION OF THE DRAWINGS

These and other features and advantages of the present invention will be better understood by reference to the following detailed description of a preferred embodiment of the invention when considered in conjunction with the accompanying drawings in which, FIG. 1 is a partial section view of a detachable balloon embolization device;

FIG. 2 is a partial section view of the distal end of the detachable balloon embolization device with the balloon removed from the distal end of the catheter;

FIG. 3 is a partial section view of the distal end of the detachable balloon embolization device with the balloon engaging the distal end of the catheter;

FIGS. 6 through 10 show a sequence of use wherein,

FIG. 6 shows the detachable balloon embolization device placed within an aneurysm of a blood vessel;

FIG. 7 shows the detachable balloon embolization device inflated to engage the walls of the aneurysm;

FIG. 8 shows the detachable balloon embolization device with adhesive applied within the outer balloon of the device;

FIG. 9 shows the detachable balloon embolization device with the balloon deflated and the volume of the aneurysm reduced; and, FIG. 10 shows the detachable balloon embolization device with the balloon detached from the catheter.

DESCRIPTION OF A PREFERRED EMBODIMENT

Figure 4:
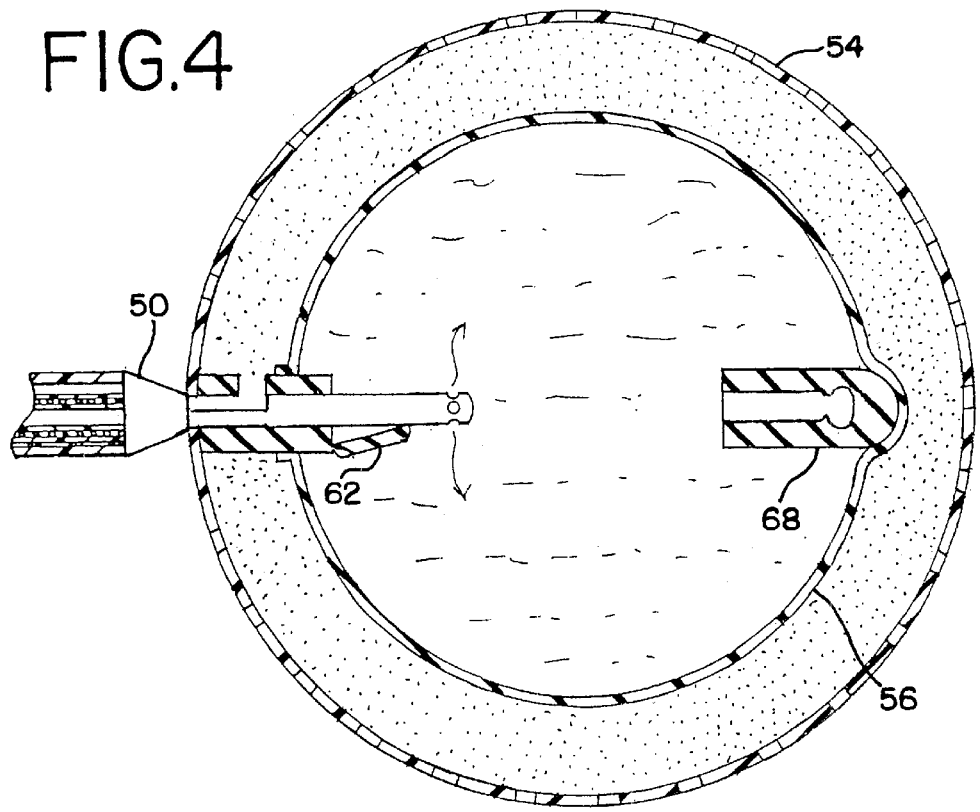
FIG. 4 is a partial section view of the detachable balloon embolization device with the balloon inflated.

Turning now to the drawings, FIG. 1 illustrates a partial section view of a catheter with a detachable balloon embolization device made in accordance with the present invention. The catheter 2 includes an outer tubular member 4, having a proximal end 6 and a distal end 8, and an inner tubular member 10, having a proximal end 12 and a distal end 14. A dual port Y-connector 16 is coupled to the proximal end 6 of the outer tubular member 4 and the proximal end 12 of the inner tubular member 10. The distal end 8 of the outer tubular member 4 and the distal end 14 of the inner tubular member 10 are adapted using a catheter adapter 50 to attach to a detachable balloon embolization device or balloon assembly 52, the details of which are described below.

As illustrated, the outer tubular member 4 includes a proximal portion 30 and a distal portion 32 of differing diameters, with the proximal portion being larger than the distal portion. In addition, the proximal portion 30 is formed from nylon having a durometer of 75 D and the distal portion 32 is formed of polyurethane having a durometer of 65 D. The reduced diameter of the distal portion 32 of the outer tubular member 4, together with the decrease in durometer, results in the distal section of the catheter being more flexible and therefore may be more easily passed through the tortuous vessels of the human body.

The inner tubular member 10 is comprised of a thin inner layer 34, a reinforcing layer 36 placed on top of the inner layer 34 and a soft outer layer 38 which surrounds and bounds the reinforcing layer 36 to the inner layer 34. The reinforcing layer 36 is comprised of a proximal reinforcing layer 40 which is formed from braided stainless steel wires and a distal reinforcing layer 42 which is formed from a single helically wound platinum wire. The soft outer layer 38 is heat bonded onto the reinforcing layer 36. Accordingly, with the proximal section of the catheter having the inner tubular member formed with a braided reinforcing layer, this section of the catheter becomes relatively stiff and has a relatively high column strength so that the catheter may be pushed into and through the vasculature of the human body. On the other hand, the distal section of the catheter is formed with the inner tubular member comprised of a single helically wound wire which, while being sufficiently stiff to resist kinking, is still very flexible and is capable of traversing tortuous vessels.

As may now be appreciated, with the balloon catheter as illustrated in FIG. 1, the proximal section of the catheter is formed with an outer tubular member portion of an increased diameter and an inner tubular member which is formed by bonding a reinforcing layer of woven stainless steel wires between two polymer layers thereby providing a proximal catheter section which exhibits the characteristic of having relatively high column strength. The distal section of the catheter is formed with an outer tubular member having a reduced outer and inner diameter and with a single helically wound wire bonded between two polymer tubular members to thereby provide a distal section which is relatively kink resistant, but still remains very flexible.

FIG. 2 illustrates a sectioned view of a preferred embodiment of a detachable balloon embolization device 52. The detachable balloon embolization device or balloon assembly 52 has an outer balloon 54 and an inner balloon 56. A valve assembly 58 extends through a wall of the inner balloon 56 and a corresponding section of the wall of the outer balloon 54. The valve assembly 58 has a passageway 60 through a cylindrical sleeve 61 which ends in a sealing valve 62. The sealing valve 62 opens when the catheter adapter 50 is inserted into the valve assembly 58 through the passageway 60. When the sealing valve 62 is open, fluid can be applied to the interior region of the inner balloon 56 through an aperture in the distal end of the catheter adapter. When the catheter adapter 50 is withdrawn from the valve assembly 58, the sealing valve 62 closes and fluid is prevented from flowing into or out of the interior region of the inner balloon 56.

The passageway 60 also includes an aperture 64 in the side wall. The aperture 64 allows for fluid communication with the interior region of the outer balloon 54. The catheter adapter 50 has a corresponding aperture which allows the lumen of the outer tubular member to communicate with the interior region of the outer balloon when the catheter adapter is fully inserted in the valve assembly 58.

The balloon assembly 52 also includes a catheter retainer mechanism 68 which is affixed to the wall of the interior region of the inner balloon 56 at a point diametrically opposite to the valve assembly 58. The retainer mechanism 68 generally takes the form of a solid cylindrical body member 70 having a generally cylindrical cavity 72 which extends inwardly from the end wall of the cylindrical body member 70. The walls of the cylindrical cavity 72 are preferably formed in a slightly convex configuration to form an inside diameter slightly less than the outside diameter of the catheter adapter 50. The catheter retainer mechanism 68 is preferably formed from a resilient material, such as a silicone composition, and the inside diameter of the convex portions of the sidewalls of the cavity 72 are of an inside diameter to frictionally engage the catheter adapter 50. Slots may be formed in the concave portions of the sidewalls of the cavity 72 to allow fluid to flow from the enlarged bulbous area 74 at the inside portion of the cavity back into the interior region of the inner balloon 56.

With the catheter of the present invention, fluid may be applied through a lumen in a side port 26 of the Y-connector 16 which communicates with the passageway between the inner tubular member 10 and the outer tubular member 4 to thereby inflate the outer balloon 54. Likewise, fluid may be applied through a lumen in a proximal port 28 of the Y-connector 16 which communicates with the passageway within the inner tubular member to thereby inflate the inner balloon 56. Preferably, the fluid is applied using a syringe (not shown) coupled to either the side port 26 or the proximal port 28 of the Y-connector 16, although other means known to the art may be employed as well.

FIG. 3 illustrates the balloon assembly 52 with the catheter adapter 50 inserted through the sealing valve assembly 58 and into the retainer mechanism 68. In this configuration, the sealing valve 62 is shown in an open position, the cylindrical sleeve 61 provides a fluid-tight seal about the outside surface of the catheter adapter 50, and the distal end of the catheter adapter 50 is retained by the resilient sidewalls of the cylindrical cavity 72.

Figure 5:
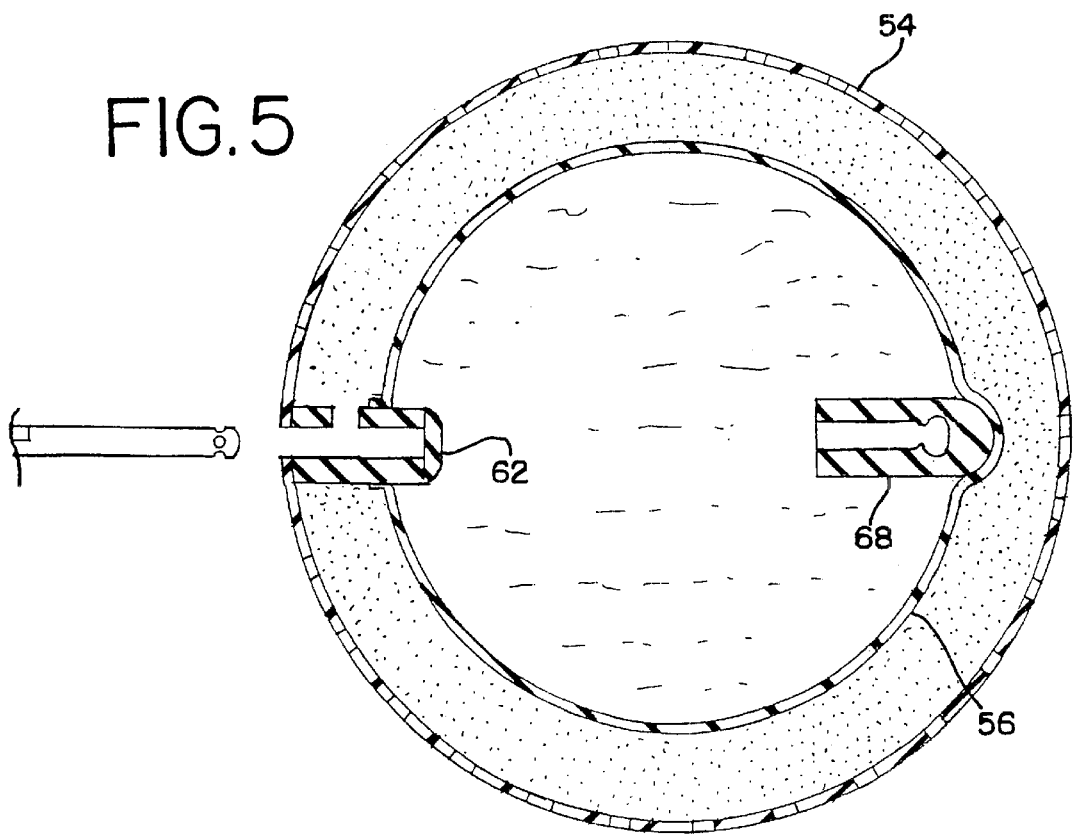
FIG. 5 is a partial section view of the detachable balloon embolization device with the balloon inflated and detached from the distal end of the catheter.

As illustrated in FIGS. 3 and 4, as fluid is applied through the catheter adapter 50, out of the aperture in the distal end of the catheter adapter, though the slots and into the inner balloon 56, the balloon begins to inflate. When the inner balloon 56 attains a certain volume of inflation, the balloon causes the retainer mechanism 68 to be moved thereby withdrawing the distal end of the catheter adapter 50 from the retainer mechanism 68. Once the catheter adapter 50 is withdrawn from the retainer mechanism 68, as shown in FIG. 5, the catheter adapter 50 may then be withdrawn from the sealing valve assembly 58 and the sealing valve 62 closes.

Figure 6:
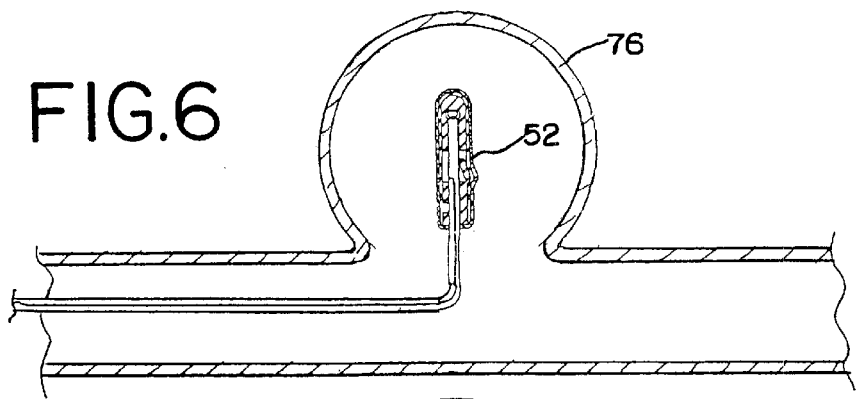
Figure 7:
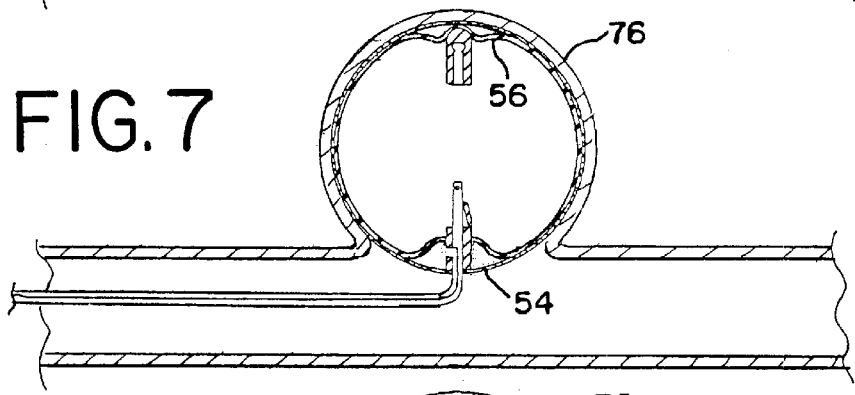

FIGS. 6 through 10 illustrate a method for using the detachable balloon embolization device just described. FIG. 6 shows the balloon assembly 52 being positioned within an aneurysm 76 of a blood vessel. The inner balloon is then inflated by applying fluid to the interior portion of the inner balloon. As the balloon inflates, it displaces the blood which has collected within the aneurysm. As shown in FIG. 7, the balloon eventually occupies substantially the entire volume of the aneurysm. The fluid used to inflate the balloon can be radiopaque to allow the inflated balloon to be floroscopically observed.

Figure 8:
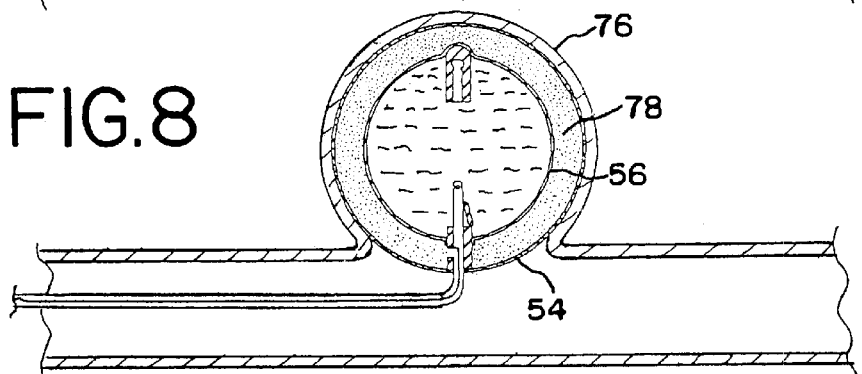
Figure 9:
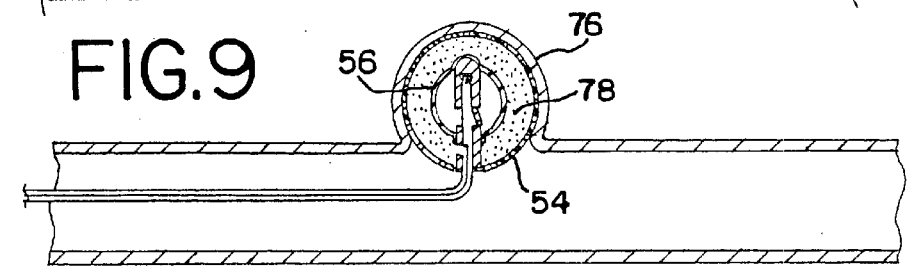

As shown in FIG. 8, once the balloon has been inflated, an adhesive material 78 is introduced into the interior region of the outer balloon. The adhesive material perfuses through the porous material which forms the outer balloon and causes the outer balloon to adhere to the aneurysm. Similarly, some adhesive remains within the outer balloon and acts to adhere the outer balloon to the inner balloon. Once the adhesive cures, the inner balloon is deflated. As shown in FIG. 9, as the inner balloon is deflated, the size of the aneurysm is reduced.

Figure 10:
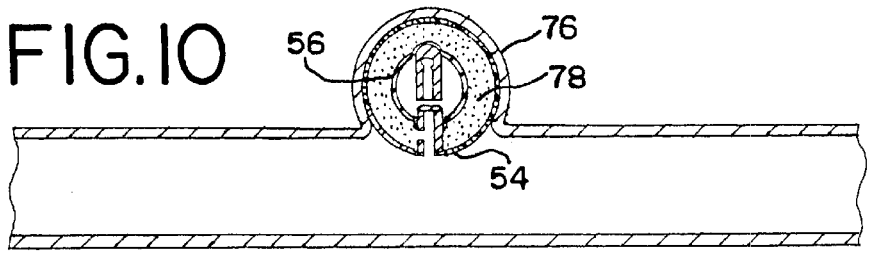

FIG. 10 shows the balloon detached from the catheter. As can be appreciated, the aperture used to inflate the outer balloon is sealed by the adhesive material which was introduced into the interior region of the outer balloon. The sealing valve, which closed when the catheter adapter was removed, prevents fluid from reentering the interior region of the inner balloon.

As is apparent, there are numerous modifications of the preferred embodiment described above that will be readily apparent to one skilled in the art. These modifications would be apparent to those having ordinary skill in the art to which this invention relates and are intended to be within the scope of the claims that follow.

What is claimed is:

1. An endovascular aneurysm occlusion device comprising:

a catheter including an outer tubular member having a proximal end, a distal end and a lumen extending therethrough, said catheter also including an inner tubular member having a proximal end, a distal end and a lumen extending therethrough, said inner tubular member being coaxially disposed within the lumen of the outer tubular member;

a balloon assembly including an outer balloon having an outer wall defining an interior region and an inner balloon having an outer wall defining an interior region, said inner balloon being disposed within the interior region of the outer balloon;

said balloon assembly also including a valve assembly, said valve assembly extending through the wall of the outer balloon and an adjacent portion of the wall of the inner balloon, said valve assembly having a passageway therethrough and a valve means disposed in the passageway, the distal end of the outer and inner tubular members of the catheter extends into the passageway, said valve means being operative to permit the passage of the catheter through the valve assembly but preventing the flow of fluid through said valve assembly when the catheter is withdrawn from said valve assembly; and, a hub having a first lumen and a second lumen, each lumen extending through a hub connector, said hub being mounted to the proximal end of the outer tubular member and the proximal end of the inner tubular member such that the first lumen of the hub is in fluid communication with the lumen of the outer tubular member and the second lumen of the hub is in fluid communication with the lumen of the inner tubular member.

2. An endovascular aneurysm occlusion device as described in claim 1, wherein the outer balloon is formed of a porous material.

3. A method for occluding an aneurysm by the use of an occlusion device comprising a balloon assembly which includes an outer balloon, an inner balloon, and a valve assembly, said outer balloon being formed from a porous material, said inner balloon being disposed within the outer balloon, said valve assembly extending through a wall of the inner balloon and an adjacent wall of the outer balloon, and a catheter having its distal end removably disposed within the valve assembly; said method comprising the steps of:

positioning the balloon assembly within an aneurysm;

inflating the inner balloon such that the inner balloon makes contact with the outer balloon to thereby force the outer balloon into contact with the aneurysm;

introducing an adhesive material into a region between the inner balloon and the outer balloon thereby causing the inner balloon to become bonded to the outer balloon;

perfusing the adhesive material through the porous material of the outer balloon thereby causing the outer balloon to become bonded to the aneurysm;

deflating the inner balloon thereby causing the outer balloon to contract which, in turn, reduces the size of the aneurysm; and, detaching the catheter from the balloon assembly thereby causing the valve assembly to close and thereby causing the inner balloon to remain in a deflated state.

* * * * *